United States Patent
Heidari et al.

(10) Patent No.: US 12,016,692 B2
(45) Date of Patent: Jun. 25, 2024

(54) SENSOR READOUT CIRCUIT FOR A BIOMAGNETISM MEASUREMENT SYSTEM

(71) Applicant: The University Court of the University of Glasgow, Glasgow (GB)

(72) Inventors: Hadi Heidari, Glasgow (GB); Siming Zuo, Glasgow (GB)

(73) Assignee: The University Court of the University of Glasgow, Glasgow (GB)

( * ) Notice: Subject to any disclaimer, the term of this patent is extended or adjusted under 35 U.S.C. 154(b) by 487 days.

(21) Appl. No.: 17/379,702

(22) Filed: Jul. 19, 2021

(65) Prior Publication Data
US 2023/0012505 A1  Jan. 19, 2023

(51) Int. Cl.
| | |
|---|---|
| A61B 5/242 | (2021.01) |
| A61B 5/00 | (2006.01) |
| G01R 33/00 | (2006.01) |
| G01R 33/09 | (2006.01) |

(52) U.S. Cl.
CPC ............ *A61B 5/242* (2021.01); *A61B 5/7203* (2013.01); *A61B 5/725* (2013.01); *G01R 33/0023* (2013.01); *G01R 33/098* (2013.01); *A61B 2562/0223* (2013.01)

(58) Field of Classification Search
CPC ....... A61B 5/242; A61B 5/7203; A61B 5/725; A61B 2562/0223; G01R 33/0023; G01R 33/098; G01R 33/0029
See application file for complete search history.

(56) References Cited

U.S. PATENT DOCUMENTS

| | | | |
|---|---|---|---|
| 5,206,602 A * | 4/1993 | Baumgartner | A61B 5/30 330/258 |
| 8,969,101 B1 * | 3/2015 | Wan | G01R 33/093 257/422 |
| 9,123,877 B2 | 9/2015 | Lei et al. | |
| 9,651,432 B2 | 5/2017 | Fuji et al. | |
| 2008/0272771 A1 * | 11/2008 | Guo | G01R 33/093 324/260 |

(Continued)

FOREIGN PATENT DOCUMENTS

| | | |
|---|---|---|
| CN | 103364543 | 10/2013 |
| EP | 3095754 | 11/2016 |

(Continued)

OTHER PUBLICATIONS

Baillet et al.; Magnetoencephalography for brain electrophysiology and imaging; Nature Neuroscience; vol. 20; No. 3; 2017; 327-39.

(Continued)

*Primary Examiner* — Peter Luong
(74) *Attorney, Agent, or Firm* — Troutman Pepper Hamilton Sanders LLP (57) ABSTRACT

A readout integrated circuit (IC) architecture for a tunnelling magnetoresistive (TMR) sensor which uses common mode feedback to achieve a performance level suitable for accurate detection of biomagnetic signals. The architecture uses a three-operational amplifier configuration with chopper stabilization. The architecture may form part of a fully integrated biomagnetic sensor electronics package that includes an array of TMR sensors together with modules for signal amplification and conditioning, data conversion and communication.

19 Claims, 4 Drawing Sheets

(56) References Cited

U.S. PATENT DOCUMENTS

| | | | | |
|---|---|---|---|---|
| 2012/0158324 A1* | 6/2012 | Romani | ............... | G01R 33/096 702/57 |
| 2017/0212188 A1* | 7/2017 | Kikitsu | ................ | G01R 33/025 |
| 2020/0170514 A1* | 6/2020 | Hui | ....................... | A61B 5/7267 |

FOREIGN PATENT DOCUMENTS

| | | |
|---|---|---|
| EP | 3167265 | 5/2017 |
| WO | 2016005325 A1 | 1/2016 |

OTHER PUBLICATIONS

Bi et al.; Power System Transient Current Sensor Based on Magnetoresistance Effect; IOP Conf. Series: Earth and Environmental Science 668; 2021; 8 pages.

Boto et al.; Moving magnetoencephalography towards real-world applications with a wearable system; Nature; vol. 555; No. 7698; 2018; 20 pages.

Djamal et al.; Giant Magnetoresistance Sensors Based on Ferrite Material and Its Applications; Magnetic Sensors—Development Trends and Applications, Chapter 6, Intech; 24 pages.

Fenici et al.; Clinical application of magnetocardiography; Expert Review of Molecular Diagnostics; vol. 5; No. 3; 2005; 291-313.

Geselowitz et al.; Magnetocardiography: an overview; IEEE Transactions on Biomedical Engineering; No. 9; 1979; 497-504.

Heidari et al.; CMOS Magnetic Sensors for Wearable Magnetomyography; 40th International Conference of the IEEE Engineering in Medicine and Biology Society (EMBC); Honolulu, HI; 2018; 2116-19.

Im et al.; Recent advances in biomagnetism and its applications; Springer, 2017; 2 pages.

Kleiner et al.; Superconducting quantum interference devices: State of the art and applications; Proceedings of the IEEE; vol. 92; No. 10; 2004; 1534-48.

Lenard et al.; Eye Tracking Simulation for a Magnetic-based Contact Lens System; 27th IEEE International Conference on Electronics, Circuits and Systems (ICECS); 2020; 3 pages.

Li et al.; Magnetoresistance Sensor with Analog Frontend for Lab-on-Chip Malaria Parasite Detection; 2021 IEEE International Symposium on Circuits and Systems (ISCAS); 5 pages.

Mackert; Magnetoneurography: theory and application to peripheral nerve disorders; Clin. Neurophysiol; vol. 115; No. 12; 2004; 2667-76.

Malmivuo et al.; Bioelectromagnetism: principles and applications of bioelectric and biomagnetic fields; Oxford University Press, USA; 1995; 642 pages.

Mohamed et al.; A Low Noise CMOS Sensor Frontend for a TMR-based Biosensing Platform; 2020 IEEE Sensors Conference; 4 pages.

Tanwear et al.; Spintonic Sensors Based on Magnestic Tunnel Junctions for Wireless Eye Movement Gesture Control; IEEE Transactions on Biomedical Circuits and Systems; vol. 14; No. 6; Dec. 2020; 3 pages.

Witte et al.; A CMOS Chopper Offset-Stabilized Opamp; IEEE Journal of Solid-State Circuits; vol. 42; No. 7; 2007; 1529-35.

Zuo et al.; High-Precision Biomagnetic Measurement System Based on Tunnel Magneto-Resistive Effect; 27th IEEE International Conference on Electronics, Circuits and Systems (ICECS); 2020; 3 pages.

Zuo et al.; Integrated Pico-Tesla Resolution Magnetoresistive Sensors for Miniaturised Magnetomyography; 42nd Annual International Conference of the IEEE Engineering in Medicine & Biology Society (EMBC); 2020; 3415-19.

Zuo et al.; Miniaturized magnetic sensors for implantable magnetomyography; Advanced Materials Technologies; vol. 5; 2020; 15 pages.

Zuo et al.; A CMOS Analog Front-End for Tunnelling Magnetoresistive Spintronic Sensing Systems; IEEE International Symposium on Circuits and Systems (ISCAS); Sapporo, Japan; 2019; 5 pages.

Zuo et al.; Device modelling of MgO-barrier tunnelling magnetoresistors for hybrid spintronic-CMOS; IEEE Electron Device Letter; vol. 39; No. 11; 2018; 2116-19.

Zuo et al.; Ultrasensitive Magnetoelectric Sensing System for pico-Tesla MagnetoMyoGraphy; IEEE Transaction on Biomedical Circuits and Systems; 2020; 14 pages.

\* cited by examiner

SENSOR READOUT CIRCUIT FOR A BIOMAGNETISM MEASUREMENT SYSTEM

FIELD OF THE INVENTION

The present invention relates to a system for measuring biomagnetism and particularly, although not exclusively, to a readout circuit for a tunnelling magnetoresistive (TMR) array used in such a system.

BACKGROUND

With the rapid progress of micro- and nano-technology, non-invasive assessment of biomagnetism has been a reliable and robust approach and its applications have been extended from clinical diagnoses to human-computer-interaction. Detecting weak biomagnetic fields derived from human active organs and tissues, mainly including Magnetocardiography (MCG), Magnetoencephalography (MEG), Magnetomyography (MMG), Magnetoneurography (MNG), requires effective methods that offer both high spatial and temporal resolutions. Conventionally, in the clinic, the activity of living tissues is recorded with bioelectricity from the surface of the skin using metal or stainless steel electrodes. However, the electric signals suffer from poor spatial resolution, which is very challenging to target specific tissues, even with high-density needle recording probes. In addition to being painful, the penetration of the needle into the muscle disturbs the muscle structure and function. Moreover, in chronic implants, such as for the motor rehabilitation, the interface between the metal contacts of the sensor and the human tissue changes over time, leading to infection and rejection by the body. Therefore, a different paradigm that enables the recording with a high spatial resolution is needed.

Biomagnetism has become an alternative method and addressed the limitation of the bioelectricity. Firstly, magnetic signals have the same temporal resolution as the electric signal but can offer significantly higher spatial resolution. Secondly, the magnetic approach does not require electric contacts during the recording and therefore, the sensor can be fully encapsulated with biocompatible materials so as to minimise the risk of infection. However, magnetically recording has remained some technical challenges for over four decades. Compared to a high temporal resolution, its spatial resolution is restrained because of some elements such as limited sensor numbers, movement artifacts, intrinsically low signal-to-noise ratio (SNR), and cancellation of background magnetic noise in real-time. Current technologies developed to detect such tiny magnetic field are exploring the use of superconducting quantum interference devices (SQUIDs) and optically-pumped magnetometers (OPMs). Both experiments are strictly limited in a large magnetically shielded room. These conventional methods are bulky, costly, consume large power and also need a temperature-controlled environment.

Nowadays, spintronic sensors based on a magnetoresistive (MR) effect revolutionise the way magnetic recording owing to their full compatibility with traditional silicon technology. These sensors can be integrated with the readout circuitry onto a standard CMOS process in sub-mm diameter substrates to eventually realize the on-chip signal conditioning, including amplification, filtering, noise and drift cancellation. This phenomenon has led to the development of the MR sensors with ultra-high sensitivity, which have gradually replaced the traditional thin-film magneto-transport devices such as Hall sensors and have the potential to detect pico-Tesla range magnetic fields, appropriate for biomagnetic signal level. In addition, the miniaturized MR sensor area can improve the resolution of fields with small distance changes. The sensor placed at a closer distance to the neural sources will provide stronger signals. The MR sensors, thereby, are suitable for array applications with a lower power requirement. Recently, giant magnetoresistive (GMR) sensors were used to record weak biomagnetic signals. However, the sensitivity of GMR sensors is in the nano-Tesla range and therefore averaging was required to enhance the SNR. Over the last decade, sensing at pico-Tesla/$\sqrt{Hz}$ level fields has become possible with the tunnelling magnetoresistive (TMR) sensors that are highly miniaturized and can be operated at room temperature using a sensor array.

SUMMARY OF THE INVENTION

At its most general, the present invention provides a readout integrated circuit (IC) architecture for a tunnelling magnetoresistive (TMR) sensor which uses common mode feedback to achieve a performance level suitable for accurate detection of biomagnetic signals. The architecture may use a three-operational amplifier configuration with chopper stabilization. The architecture may form part of a fully integrated biomagnetic sensor electronics package that includes an array of TMR sensors together with initial signal amplification and conditioning, data conversion and signal processing. Such a package may facilitate real-time measurement.

According to one aspect of the invention, there is provided a biomagnetism sensing system. The system comprises a magnetic sensor comprising a plurality of sensor elements arranged in a full Wheatstone bridge configuration. The system comprises a readout circuit having a differential amplifier that is configured to receive differential input signals from the magnetic sensor. The differential amplifier generates an amplified measurement signal from the received differential input signals. A low pass filter is configured to remove high frequency components from the amplified measurement signal to provide a filtered signal. The filtered signal is received by a microcontroller, which is arranged to process the filtered signal and generate an output signal. The differential amplifier includes a common-mode feedback (CMFB) circuit configured to eliminate a common-mode current component from the differential input signals. In conjunction with the filter, the configuration of the differential amplifier can enable the readout circuit of the system to exhibit properties suitable for recording biomagnetic signals. In particular, the use of a CMFB circuit enables an input-referred voltage noise for the readout circuit to be of the order of nV/$\sqrt{Hz}$ over a frequency range suitable for biomagnetic signal detection.

Each of the sensor elements in the magnetic sensor may be an array of spintronic sensing elements. Using an array of sensing elements assists in achieving optimal noise performance. In one example, each spintronic sensing element comprises a tunnelling magnetoresistive (TMR) element. The array of spintronic sensing elements may be fabricated on a substrate, e.g. a silicon substrate, using conventional CMOS microfabrication techniques. Each spintronic sensing element may have a size equal to or greater than 100 μm×100 μm. Using relatively large area sensing elements can also assist in optimising the noise performance of the system.

The differential amplifier, the bandpass filter and microcontroller may be mounted on a common substrate (e.g.

made from silicon or the like) to provide an integrated front end processing package for the system. The spintronic sensing elements may be fabricated on the common substrate, whereby the magnetic sensor and front end processing form a monolithic integrated circuit.

A first variable resistance may be connected at the input to the differential amplifier. The microcontroller may be configured to adjust the first variable resistance to control a gain of the differential amplifier. The system may further comprise an input buffer amplifier stage connected between the magnetic sensor and the differential amplifier. The input buffer stage may comprise a pair of operational amplifiers, each operational amplifier configured as a buffer amplifier for a respective differential input signal. A second variable resistance may be connected at the input to the input buffer amplifier stage. The microcontroller may be configured to adjust the second variable resistance to control a gain of the input buffer amplifier stage. The control of the variable resistance may be achieved through a digital-to-analog converter (DAC). For example, the microcontroller may output a 5-bit gain control signal which the DAC converts to a suitable setting signal for the variable resistance. The variable resistance may be provided by one or more variable resistors, whose behaviour is essentially programmable by the microcontroller via the setting signal. In this way, the gain of the system may be controlled to be suitable for a particular use context. The gain may be adjustable in a range from 20 to 80 dB whilst maintaining the low noise performance discussed above.

The pair of operational amplifiers in the input buffer amplifier stage may have a chopper-stabilized input.

The two stage fully differential amplifier uses chopping to eliminate the input offset and low frequency noise by means of chopper switches which enable a modulation-demodulation technique. Referring to the system architecture diagram (FIG. 3), the input chopper in a NMOS input differential pair is modulated up to the chopping frequency. At the output chopping stage, the input signal is synchronously demodulated back to its original frequency and simultaneously the offset and 1/f noise of the amplifier input stage are modulated to the chopping frequency. The use of chopper stabilization at the input buffer amplifier stage ensures low noise by eliminating upmodulating offset and low-frequency flicker noise. The differential amplifier has a chopping output to reintegrate the signal. The chopping frequency is usually between a few hundred Hz and several kHz, and it should be noted that because this is a sampling system, the input frequency must be much less than one-half the chopping frequency to prevent errors due to aliasing.

The system may comprise a computing device in communication with the microcontroller to receive and process the output signal. The computing device may operate as a back end processor, e.g. to analyse the output signal to identify, characterize or quantify a biomagnetic signal. The computing device may be any device with suitable processing capability, e.g. a smartphone, tablet, laptop or the like. The computer device may be located remotely from the readout circuit. For example, the readout circuit may include a wireless communication module connected to the microcontroller and configured to transmit wirelessly the output signal from the microcontroller to the computing device.

The system may operate in a bandwidth of 1 Hz to 1 kHz. The low pass filter may therefore have a cut-off frequency equal to or less than 1 kHz. However, it may be desirable for the cut-off frequency to be lower to further optimise performance. For example, the cut-off frequency may be equal to or less than 500 Hz, e.g. in a range from 300 Hz to 500 Hz. The low pass filter may be a 20th order Butterworth filter.

The system may further comprise an analog-to-digital convertor (ADC) arranged at the output of the low pass filter to convert the filtered signal into digital data. The ADC may be an 18-bit successive approximation register ADC, which has the benefits of high speed, high accuracy, low-power and low-cost.

The readout circuit may comprise an inbuilt power source (e.g. battery of the like). The microcontroller may be configured to control a power management module that sets a rail voltage across the Wheatstone bridge.

In another aspect, the invention provides a readout circuit for a biomagnetism sensor, the readout circuit comprising: a differential amplifier configured to receive differential input signals from a magnetic sensor and generate an amplified measurement signal from the received differential input signals; a bandpass filter configured to remove high frequency components from the amplified measurement signal to provide a filtered signal; and a microcontroller configured to receive and process the filtered signal and generate a output signal, wherein the differential amplifier includes a common-mode feedback circuit configured to eliminate a common-mode current component from the differential input signals.

In a further aspect, the invention provides a wearable biosensor comprising: a body-mountable part and a biomagnetism sensing system as set out above mounted on the body-mountable part. The body-mountable part may be an armband, wristwatch, or pair of eyeglasses. The body-mountable part may be configured to bring the magnetic sensor into close proximity with the magnetic signals it is intended to detect.

The invention includes the combination of the aspects and preferred features described except where such a combination is clearly impermissible or expressly avoided.

SUMMARY OF THE FIGURES

Embodiments of the invention will now be discussed with reference to the accompanying figures.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figure 1:
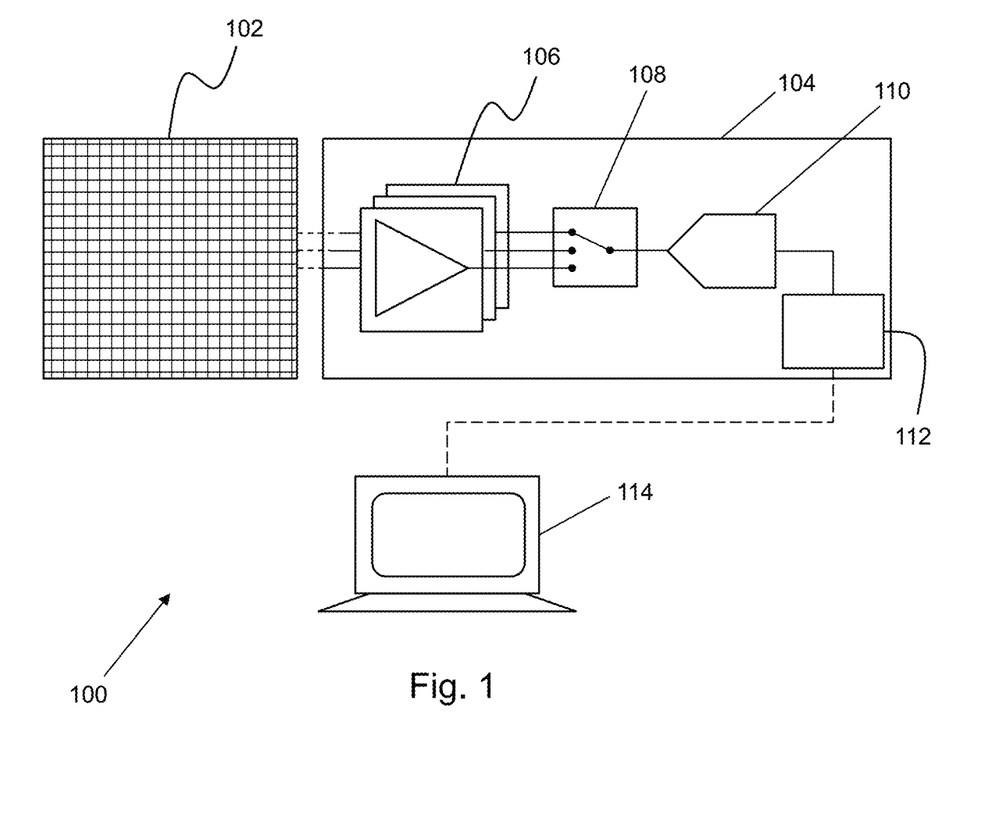
FIG. 1 is a schematic diagram showing a biomagnetism measurement system that is an embodiment of the invention.

FIG. 1 shows a biomagnetism measurement system 100 that is an embodiment of the invention. The system 100 comprises a magnetic sensor 102 that comprises a plurality of tunnelling magnetoresistive (TMR) elements configured in an array, e.g. fabricated on a silicon substrate using conventional CMOS microfabrication techniques. The system may further include an integrated signal processing package 104 that is preferably fabricated on a common substrate with the magnetic sensor 102. In this example, the signal processing package 104 comprises an analog readout circuit 106 configured to generate an analog output that is delivered to an analog-to-digital converter (ADC) 110. The ADC 110 in connected to a microcontroller 112 that includes a wireless communication module arranged to communicate a digital output signal to a remote device 114 for analysis. In this example, the analog readout circuit 106 is configured as a plurality of modules that are connectable to the ADC 110 by a multiplexer 108.

Each TMR sensor on the array comprises two layers of ferromagnetic material separated by a very thin insulation layer. The top layer is defined as a free layer since its magnetization direction can be changed freely, and the bottom layer is called a pinned layer due to its fixed magnetization orientation when the sensor is fabricated. The sensor is configured to permit a tunnelling effect in which electrons can pass through the insulating material under certain condition, which in turn causes the structure to exhibit spin-related magnetoresistive properties at room temperature.

The response of a TMR sensor corresponds to a change in resistance across the device with variation in magnetic field. For biomagnetic measurement, it is desirable for the response to be linear and hysteresis-free. Typically, optimal noise performance is obtained with large arrays of large area sensors. In the example discussed herein, 1102 TMR sensors are connected as 38 rows and 29 columns in series to minimize sensor 1/f noise. Each TMR element was formed from the following stack of layers (nm) [5 Ta/25 CuN]×6/5 Ta/5 Ru/20 IrMn/2 CoFew/0.85 Ru/2.6 CoFe$_{40}$B$_{20}$/MgO [9 kΩ·µm2]/2 CoFe$_{40}$B$_{20}$/0.21 Ta/4 NiFe/0.20 Ru/6 IrMn/2 Ru/5 Ta/10 Ru. The size of each TMR element is 100×100 µm. The array is electrical connect to electrode pads through which it is connected to the remaining electronics.

A Wheatstone bridge structure is employed to minimize the temperature drift and also to nullify the output signal in the absence of any applied magnetic field. In the examples discussed herein, four TMR sensor arrays of the type discussed above are arranged in a full Wheatstone bridge configuration. For a bias current of 20 mA, the measured linear range of the sensor is approximately −1 Oe to 1 Oe. With the full bridge setup, the measured resistance variation of each TMR sensor is 280 Ωµm$^2$/Oe. Thus, for 1102 elements with the area of 100×100 µm$^2$, the sensitivity is calculated as ~0.617 V/Oe.

Figure 2:
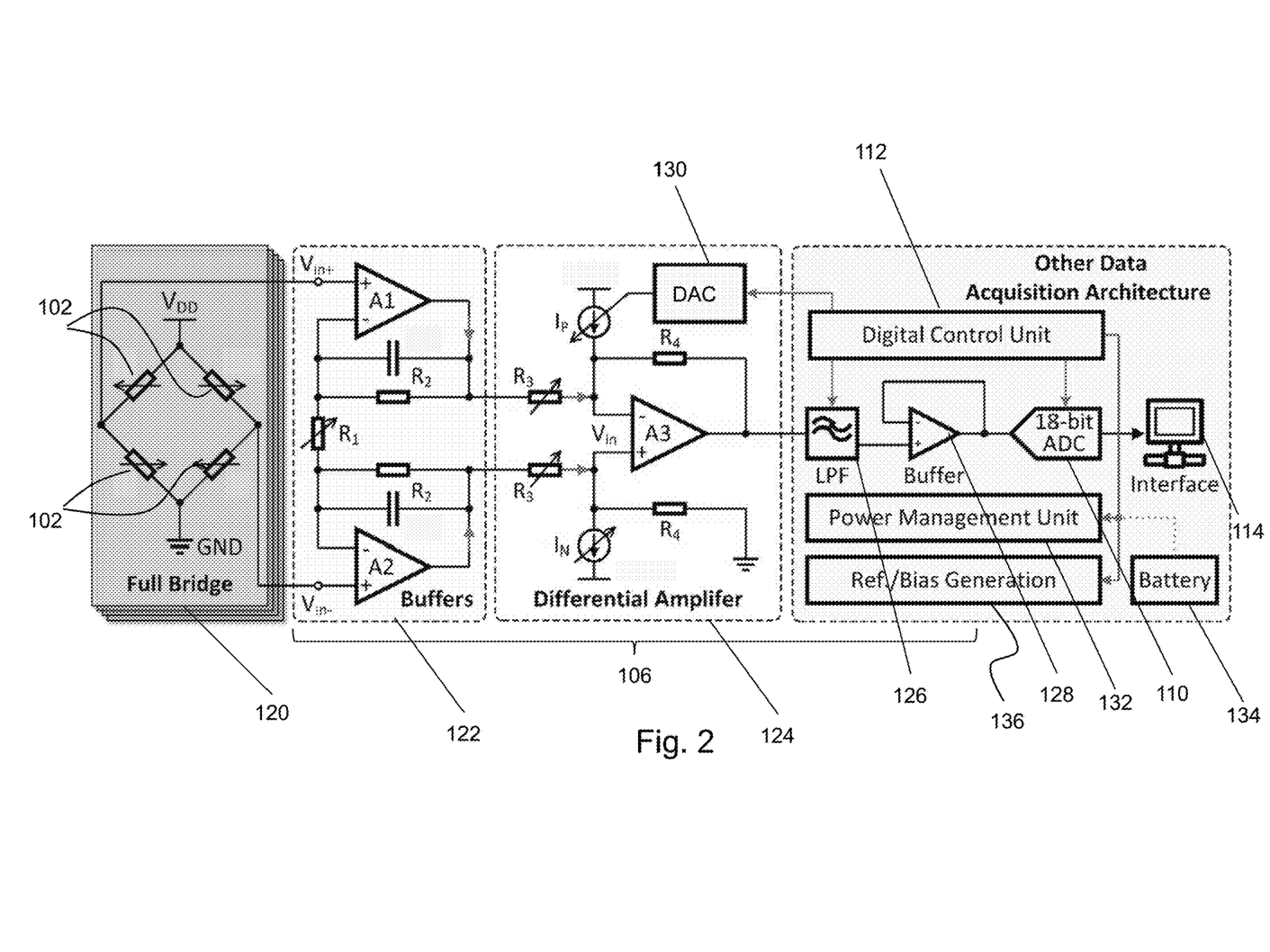
FIG. 2 is a schematic diagram showing a readout circuit architecture that can be used in the biomagnetism measurement system of FIG. 1.

FIG. 2 is a schematic diagram of the analog readout circuit 106 of FIG. 1, together with the control circuitry associated therewith. The sensor 102 discussed above may comprise a plurality of TMR sensor arrays arranged in a full Wheatstone bridge circuit 120, which provide differential input signals V$_{in+}$ and V$_{in−}$ to the readout circuit 106. The readout circuit itself comprises an input buffer stage 122 followed by a differential amplifier stage 124 and finally a low pass filter (LPF) 126 whose output is received by the ADC via a buffer 128.

The input buffer stage 122 and differential amplifier stage 124 are implemented using a three operational amplifier architecture. Two low noise input amplifiers A1, A2 are used in the input buffer stage 122. A third amplifier A3 is used in the differential amplifier stage 124. As described in more detail below, this architecture can be configured to achieve a high input impedance and excellent linearity, as well as extend the input range by using rail-to-rail input stages.

The microcontroller 112 is arranged to generate control signals for the readout circuit 106. One control signal may be used to set the gain of input buffer stage 122 through adjustment of variable resistance R$_1$, which is connected to the microcontroller 112 through a digital-to-analog converter (DAC) 130. Similarly, another control signal may be used to set the gain of differential amplifier stage 124 through adjustment of variable resistance R$_3$. In the latter case, the output offset of the three-operational amplifier is adjustable using a digital-to-analog converter (DAC) connected to the input of the fully differential amplifier A3. The DAC 130 may thus set the currents I$_P$ and I$_N$ to adjust the resistance R$_3$. The microcontroller 112 may also generate a common-mode feedback (CMFB) control signal to set the bias current of the differential amplifier stage 124, as discussed in more detail below. The CMFB control signal may be determined by a CMFB circuit 136 that is configured to generate values for a reference signal and bias signal as discussed below.

The transfer function of the proposed three-operational amplifier structure including the DAC operation is expressed as $$V_{out} = \left(1 + \frac{2R_2}{R_1}\right)\left(\frac{R_4}{R_3}\right)(V_{in+} - V_{in-}) + R_4(I_P + I_N)$$

As discussed with reference to FIG. 1, the microcontroller 112 is in communication with an ADC 110 which can communicate with a remote device 114 via any suitable (wired or wireless) interface.

The microcontroller 112 is also in communication with a power management unit 132 to use power from a power source (such as a battery 134) to apply the necessary rail voltages.

Figure 3:
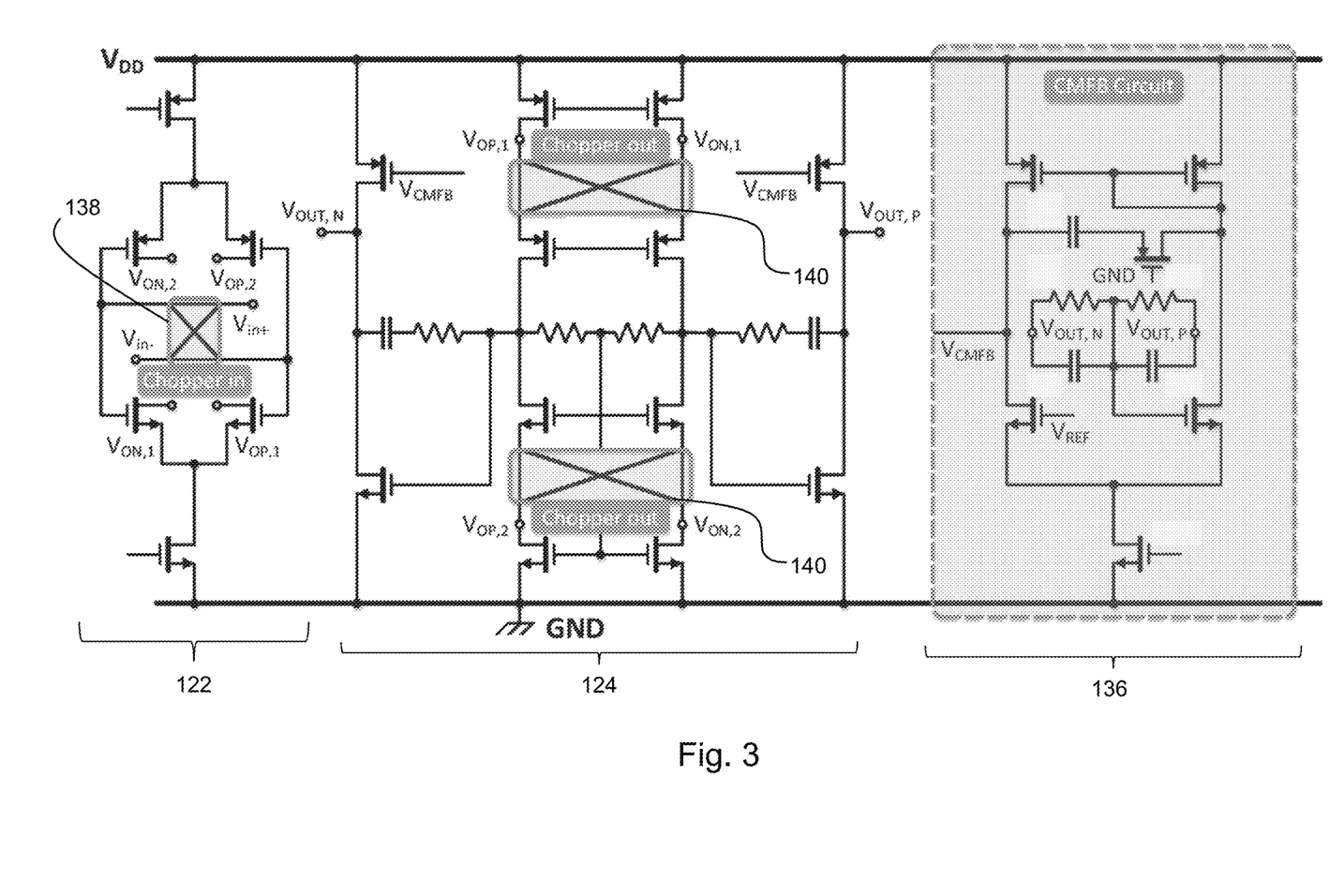
FIG. 3 is a schematic circuit diagram of a readout circuit having chopper stabilization and common-mode feedback that is an embodiment of the invention.

FIG. 3 shows a schematic circuit diagram of the input buffer stage 122 and differential amplifier stage 124 to illustrate how chopper stabilization and common-mode feedback can be used to optimise the performance of the readout circuit. The schematic circuit diagram of FIG. 3 shows a transistor arrangement for the input buffer, differential amplifier and CMFB circuit. The channel size and W/L ratio of the transistors can be chosen to obtain a desired current flow through the transistors in a conventional manner.

The two stage fully differential amplifier uses chopping to eliminate the input offset and low frequency flicker noise by means of chopper switches which enable a modulation-demodulation technique. The two amplifiers A1, A2 in the input buffer stage 122 have an input chopper switch 138 that modulates the differential input signals V$_{in+}$ and V$_{in−}$ up to a chopping frequency, which facilitates elimination of upmodulating offset and low-frequency flicker noise. The amplifier A3 in the differential amplifier stage 124 has a chopping output stage configured to reintegrate the signal. The chopping output stage comprises chopper switches 140 arranged to synchronously demodulate the signal back to its original frequency, whilst causing offset and 1/f noise of the amplifier input stage to be modulated to the chopping frequency. The chopper switches driven by respective control signals from the microcontroller, which implements a suitable modulation/demodulation process. The chopping frequency is typically selected to be between a few hundred Hz and several kHz. The chopping frequency is selected to be greater than (at least double) the sampling frequency of the ADC 110 to prevent errors due to aliasing.

The common-mode feedback (CMFB) circuit 136 is employed to maintain a DC voltage output. The CMFB circuit 136 operates to stabilize the common-mode voltage by adjusting the common-mode output currents. In this example, the CMFB circuit 136 is configured to detect the common-mode voltage by obtaining an average of the differential output voltages $V_{OUT,N}$, $V_{OUT,P}$ from the amplifier A3, compare the obtained average with a reference voltage $V_{REF}$, and return the difference voltage $V_{CMFB}$ between the average and the reference to the bias network of the differential amplifier stage 124. There the difference voltage $V_{CMFB}$ is converted to a common-mode output current to adjust the common-mode voltage. As a result, it cancels the output common-mode current components and fixes the DC outputs to a desired level. Typically the reference voltage $V_{REF}$ may be set to be half the rail voltage (i.e. $V_{DD}/2$).

Returning to FIG. 2, following chopper and CMFB stabilization, the output voltage $V_{OUT}=V_{OUT,N}-V_{OUT,P}$ of the differential amplifier stage 124 is passed through the LPF 126, which in this example is a high-order filter that adopts a Sallen-key topology with a cut-off frequency from 300 to 500 Hz. In other examples, the LPF 126 may comprise a 20th-order Butterworth filter have a bandpass region of 30 to 300 Hz.

The filtered signal is converted into digital data through the ADC 110, which in this example is an 18-bit successive approximation register ADC that offers high speed, high accuracy, low-power and low-cost.

Figure 4A:
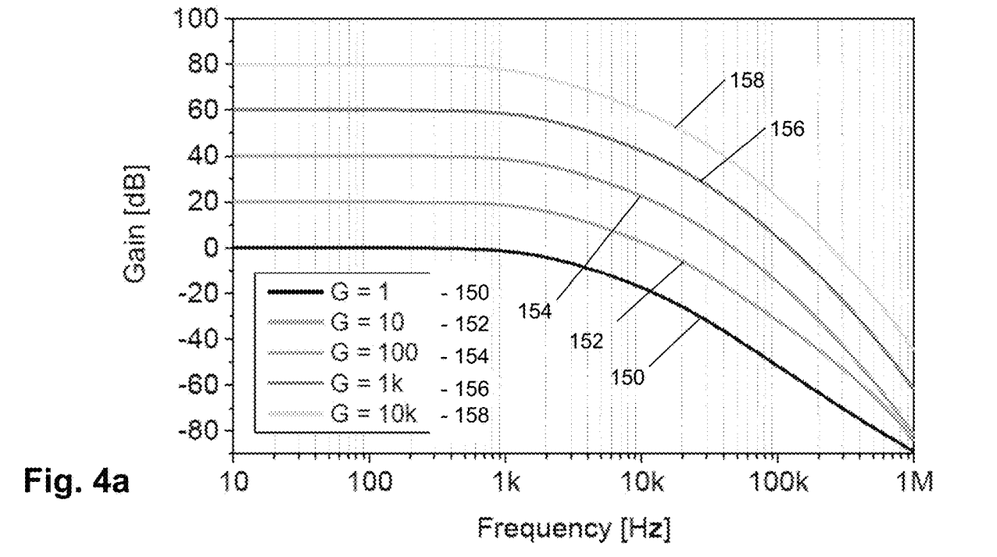
FIG. 4a is graph showing simulated transfer functions of gain for the readout circuit of FIG. 3.
Figure 4B:
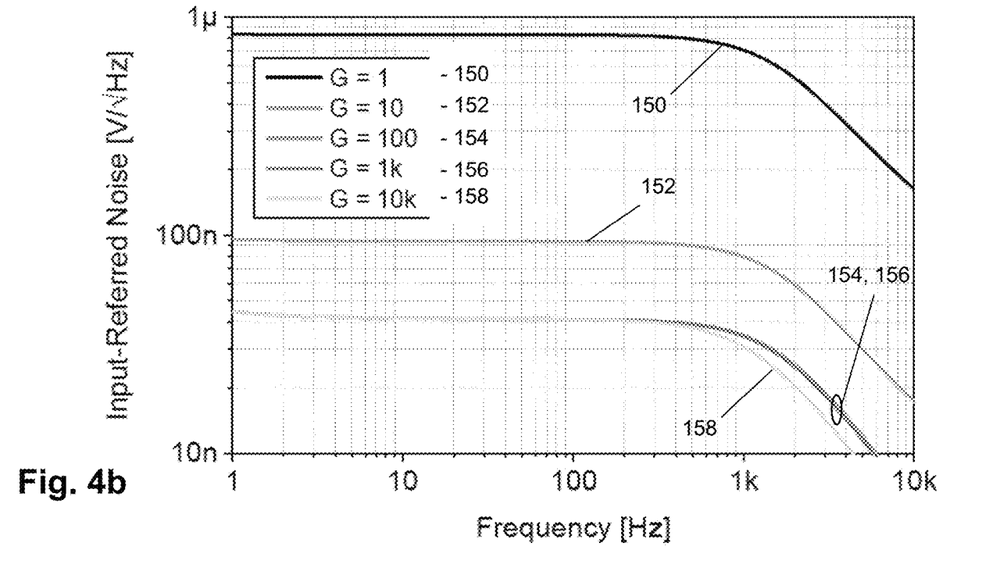
FIG. 4b is graph showing simulated transfer functions of input-referred noise gain for the readout circuit of FIG. 3.

The readout circuit design discussed above was simulated in a standard CMOS 0.18 μm technology to achieve acceptable performance, in terms of linearity, offset and noise. The Wheatstone bridge was modelled by COMSOL based on a finite element method and then the parameter of variable resistance was defined using Verilog-A language. FIG. 4z and FIG. 4b show a pair of graphs that illustrate gain and noise performance of the simulated readout circuit. The input impedance is extremely high (approximately 109Ω). The input bias current is very low (about 10 nA), which ensures very little changes with varying input voltage.

The graph shown in FIG. 4a illustrates the behaviour of differential mode gain of the readout circuit with detected frequency. With a supply voltage of 1.8 V, the DC gain and the bandwidth are 80 dB and 1 kHz with a phase margin of 62.5 degree. The common-mode rejection ratio can reach 108 dB to minimize the noise from strong electromagnetic interference.

The graph shown in FIG. 4b illustrate the behaviour of input-referred voltage noise versus frequency. It can be seen that the readout circuit achieves a noise performance of 44.6 nV/√Hz with low-pass filtering at a cut-off frequency of 1 kHz. The frequency range is well suited to biomagnetic signals, and thus the readout circuit may be particularly appropriate for use in high-resolution and low-noise biosignal recording. The noise increases slightly in the low-frequency domain due to 1/f noise, which affect becomes more pronounced in gains less than 10.

The simulation also indicated that filters having a lower cut-off frequency tend to produce minimum noise, and are therefore preferred for high-precision measurements.

In summary, the discussion above presents a low-noise and high-precision three-operational amplifier architecture readout IC for TMR sensors with a chopper stabilization and CMFB technique. A simulation of the circuit in 0.18 μm CMOS shows that it realizes good performances in respect of gain, linearity, power consumption, and noise level to record biomagnetic signals. It dissipates 58 μW of power using a 1.8 V supply voltage. The amplifier gain may adjustable between 20 and 80 dB using two 5-bit programmable resistors. A particular advantage of the readout circuit is the combination of an ultralow input-referred voltage density over a preferred frequency detection range (44.6 nV/√Hz in the range 1 Hz to 1 kHz) with a very small input bias current (10 nA). These advantages can enable high temporal and spatial resolution measurements to be obtained, which can be used to identify, characterize and quantify biomagnetic signals.

It may be recognised that the readout circuitry is capable of use in a variety of biomagnetic sensing applications. In one example, system may form part of a wearable biosensor, e.g. having a body-mountable part, such as an armband or patch, suitable for measurement of biomagnetic signals within a user's muscle. In such an example, the detected magnetic signal is a biosignal, i.e. due to electric current flow in the body itself. However, in other examples, the detected magnetic signal may be indirectly generated, e.g. through movement of magnets that are configured to move with parts of the body.

For example, one use of the invention may be to detect the movement of magnets embedded in a contact sensor in order to determine a direction of eye movement. In this scenario, the biomagnetism measurement system discussed above may be mounted within the frame of a pair of eyeglasses, such that movement of the magnets (with the eyeball) relative to the frame cause detectable changes in the resistance of the TMR sensors. By suitable positioning of a plurality of TMR sensor arrays on the frame of the eyeglasses, it becomes possible to associate certain responses with particular eye movements. This arrangement may make possible a gesture recognition system that operates through eye movement alone. The TMR-sensor based system disclosed herein may be particular suitable for a wearable device owing to their excellent sensitivity, lower bias current and comparably lower sensor size. Another advantage of using a TMR sensor for eye gesture detection is its inability to detect ultra-low fields from skeletal muscles. This is the case because the sensor is not attached to the face to detect weak magnetic fields, unlike in electrooculography, where artefacts generated by eyelid movement, blinking and facial muscle activation tend to interfere with eye movement recordings.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

The following publications are cited to more fully describe and disclose the invention and the state of the art to which the invention pertains. The entirety of each of these references is incorporated herein.

J. Malmivuo and R. Plonsey, Bioelectromagnetism: principles and applications of bioelectric and biomagnetic fields. Oxford University Press, USA, 1995.

D. B. Geselowitz, 'Magnetocardiography: an overview', IEEE Transactions on Biomedical Engineering, no. 9, pp. 497-504, 1979.

R. Fenici, D. Brisinda, and A. M. Meloni, 'Clinical application of magnetocardiography', Expert Review of Molecular Diagnostics, vol. 5, no. 3, pp. 291-313, 2005.

S. Baillet, Magnetoencephalography for brain electrophysiology and imaging', Nature Neuroscience, vol. 20, no. 3, pp. 327-339, 2017.

E. Boto et al., 'Moving magnetoencephalography towards real-world applications with a wearable system', Nature, vol. 555, no. 7698, p. 657, 2018.

S. Zuo, H. Heidari, D. Farina, and K. Nazarpour, 'Miniaturized magnetic sensors for implantable magnetomyography', Advanced Materials Technologies, no. 2000185, 2020.

S. Zuo et al., 'Ultrasensitive Magnetoelectric Sensing System for pico-Tesla MagnetoMyoGraphy', IEEE Transaction on Biomedical Circuits and Systems, 2020.

B.-M. Mackert, Magnetoneurography: theory and application to peripheral nerve disorders', Clin. Neurophysiol., vol. 115, no. 12, pp. 2667-2676, 2004.

C.-H. Im, S. C. Jun, and K. Sekihara, 'Recent advances in biomagnetism and its applications'. Springer, 2017.

R. Kleiner, D. Koelle, F. Ludwig, and J. Clarke, 'Superconducting quantum interference devices: State of the art and applications', Proceedings of the IEEE, vol. 92, no. 10, pp. 1534-1548, 2004.

S. Zuo, K. Nazarpour, and H. Heidari, 'Device modelling of MgO-barrier tunnelling magnetoresistors for hybrid spintronic-CMOS', IEEE Electron Device Letter, vol. 39, no. 11, pp. 1784-1787, 2018.

H. Heidari, S. Zuo, A. Krasoulis, and K. Nazarpour, 'CMOS Magnetic Sensors for Wearable Magnetomyography', 2018 40th International Conference of the IEEE Engineering in Medicine and Biology Society (EMBC), Honolulu, HI, 2018, pp. 2116-2119.

J. F. Witte, K. A. A. Makinwa, and J. H. Huijsing, 'A CMOS Chopper Offset-Stabilized Opamp', IEEE Journal of Solid-State Circuits, vol. 42, no. 7, pp. 1529-1535, 2007.

S. Zuo, H. Fan, K. Nazarpour, and H. Heidari, 'A CMOS Analog Front-End for Tunnelling Magnetoresistive Spintronic Sensing Systems', 2019 IEEE International Symposium on Circuits and Systems (ISCAS), Sapporo, Japan, 2019, pp. 1-5.

The invention claimed is:

1. A biomagnetism sensing system comprising:
a magnetic sensor comprising a plurality of sensor elements arranged in a full Wheatstone bridge configuration;
a differential amplifier configured to receive differential input signals from the magnetic sensor and generate an amplified measurement signal from the received differential input signals;
a low pass filter configured to remove high frequency components from the amplified measurement signal to provide a filtered signal;
a microcontroller configured to receive and process the filtered signal and generate an output signal; and
an input buffer amplifier stage connected between the magnetic sensor and the differential amplifier;
wherein the differential amplifier includes a common-mode feedback circuit configured to eliminate a common-mode current component from the differential input signals;
wherein the input buffer amplifier stage comprises:
a pair of operational amplifiers, each operational amplifier configured as a buffer amplifier for a respective one of the differential input signals, and
a chopper-stabilized input provided by an input chopper switch connected between the differential input signals and configured to modulate the differential input signals.

2. The biomagnetism sensing system of claim 1, wherein each of the plurality of sensor elements is an array of spintronic sensing elements.

3. The biomagnetism sensing system of claim 2, wherein the spintronic sensing elements comprises tunnelling magnetoresistive (TMR) elements.

4. The biomagnetism sensing system of claim 1, wherein the differential amplifier, low pass filter and microcontroller are fabricated on a common substrate.

5. The biomagnetism sensing system of claim 4, wherein the plurality of sensor elements are fabricated on the common substrate.

6. The biomagnetism sensing system of claim 1 further comprising a variable resistance connected at the input to the differential amplifier, wherein the microcontroller is configured to adjust the variable resistance to control a gain of the differential amplifier.

7. The biomagnetism sensing system of claim 1, wherein the differential amplifier has an integrated chopping output to reintegrate chopped differential input signals into the amplified measurement signal.

8. The biomagnetism sensing system of claim 1 further comprising a variable resistance connected to between negative feedback connections of the operational amplifiers of the input buffer amplifier stage, wherein the microcontroller is configured to adjust the variable resistance to control a gain of the input buffer amplifier stage.

9. The biomagnetism sensing system of claim 8 wherein the variable resistance comprises a 5-bit programmable resistor, and the amplifier gain of the input buffer amplifier stage and the differential amplifier is adjustable between 20 dB and 80 dB.

10. The biomagnetism sensing system of claim 1 further comprising a computing device in communication with the microcontroller to receive and process the output signal.

11. The biomagnetism sensing system of claim 10 further comprising a wireless communication module configured to transmit wirelessly the output signal from the microcontroller to the computing device.

12. The biomagnetism sensing system of claim 1, wherein the low pass filter has a cut-off frequency equal to or less than 500 Hz.

13. The biomagnetism sensing system of claim 1, wherein the low pass filter is a 20th order Butterworth filter.

14. The biomagnetism sensing system of claim 1 wherein each of the operational amplifiers of the input buffer stage have negative feedback including a capacitor for integrating the respective differential input signals.

15. A readout circuit for a biomagnetism sensor, the readout circuit comprising:
- a differential amplifier configured to receive differential input signals from a magnetic sensor and generate an amplified measurement signal from the received differential input signals;
- a bandpass filter configured to remove high frequency components from the amplified measurement signal to provide a filtered signal;
- a microcontroller configured to receive and process the filtered signal and generate an output signal, and
- an input buffer amplifier stage connected at the input to the differential amplifier,
- wherein the differential amplifier includes a common-mode feedback circuit configured to eliminate a common-mode current component from the differential input signals,
- wherein the input buffer amplifier stage comprises a pair of operational amplifiers, each operational amplifier configured as a buffer amplifier for a respective one of the differential input signals, and a chopper-stabilized input provided by an input chopper switch connected between modulate the differential input signals and configured to modulate the differential input signals.

16. The readout circuit of claim 15 further comprising a variable resistance connected at the input to the differential amplifier, wherein the microcontroller is configured to adjust the variable resistance to control a gain of the differential amplifier.

17. The readout circuit of claim 15, wherein the differential amplifier has an integrated chopping output to reintegrate the chopped differential input signals into the amplified measurement signal.

18. The readout circuit of claim 15 further comprising a variable resistance connected between negative feedback loops of the operational amplifiers of the input buffer amplifier stage, wherein the microcontroller is configured to adjust the variable resistance to control a gain of the input buffer amplifier stage.

19. A wearable biosensor comprising:
- a body-mountable part; and
- a biomagnetism sensing system mounted on the body-mountable part, wherein the biomagnetism sensing system comprises:
  - a magnetic sensor comprising a plurality of sensor elements arranged in a full Wheatstone bridge configuration;
  - a differential amplifier configured to receive differential input signals from the magnetic sensor and generate an amplified measurement signal from the received differential input signals;
  - a low pass filter configured to remove high frequency components from the amplified measurement signal to provide a filtered signal;
  - a microcontroller configured to receive and process the filtered signal and generate a output signal; and
  - a chopper-stabilized input buffer amplifier stage connected at the input to the differential amplifier,
- wherein the differential amplifier includes a common-mode feedback circuit configured to eliminate a common-mode current component from the differential input signals, and
- wherein the input buffer amplifier stage comprises a pair of operational amplifiers, each operational amplifier configured as a buffer amplifier for a respective one of the differential input signals, and a chopper-stabilized input provided by an input chopper switch connected between modulate the differential input signals and configured to modulate the differential input signals.

* * * * *